United States Patent [19]
Yang

[11] Patent Number: 5,109,427
[45] Date of Patent: Apr. 28, 1992

[54] FINGERPRINT RECOGNITION DEVICE USING A HOLOGRAM

[75] Inventor: Keun Y. Yang, Seoul, Rep. of Korea

[73] Assignee: Goldstar Co., Ltd., Seoul, Rep. of Korea

[21] Appl. No.: 611,850

[22] Filed: Nov. 13, 1990

[30] Foreign Application Priority Data

Nov. 13, 1989 [KR] Rep. of Korea ............... 16436/1989

[51] Int. Cl.$^5$ .................................................. G06K 9/00
[52] U.S. Cl. ......................................... 382/4; 382/31; 356/348; 359/15; 359/561
[58] Field of Search ...................... 382/4, 31; 250/227; 356/71, 347, 348; 350/376, 162.12, 162.13

[56] References Cited

U.S. PATENT DOCUMENTS

| | | | |
|---|---|---|---|
| 3,716,301 | 2/1973 | Caulfield et al. | 350/162.13 |
| 3,799,643 | 3/1974 | Mailer | 350/3.8 |
| 4,174,179 | 11/1979 | Tschudi et al. | 350/162.13 |
| 4,681,435 | 7/1987 | Kubota et al. | 356/71 |
| 4,785,171 | 11/1988 | Dowling, Jr. et al. | 382/4 |
| 4,876,725 | 10/1989 | Tomko | 382/4 |
| 4,925,300 | 5/1990 | Rachlin | 356/71 |

*Primary Examiner*—David K. Moore
*Assistant Examiner*—Yon Jung
*Attorney, Agent, or Firm*—Birch, Stewart, Kolasch & Birch

[57] ABSTRACT

A fingerprint recognition device is disclosed which is capable of making a more definite fingerprint recognition by using a hologram. The device includes a laser for emitting light, a collimator for making the light travel in parallel, and a tetragonal prism for forming a fingerprint image on it all of which are arranged along the first optical axis. A hologram is provided for shifting the position of the fingerprint image to a second optical axis, an image-forming lens for forming the fingerprint image, and an area CCD for converting the fingerprint image to electrical signals are arranged along the second optical axis. The area CCD is connected to a circuit which amplifies and analyzes the electrical signals. Accordingly, a virtual image of a fingerprint is shifted onto the optical axis of the image-forming lens by the hologram so as to be formed as a virtual image, the virtual image is formed on the area CCD by the image-forming lens to generate electrical signals according to the fingerprint image. The electrical signals are transferred to the circuit which amplifies and analyzes the signals, and then the fingerprint is recognized.

5 Claims, 2 Drawing Sheets

FINGERPRINT RECOGNITION DEVICE USING A HOLOGRAM

BACKGROUND OF THE INVENTION

The present invention relates to a fingerprint recognition device, and more particularly to a fingerprint recognition device capable of making a more definite fingerprint recognition by using a hologram.

A conventional fingerprint recognition device as shown in FIG. 1 consists of:

an LED(liquid electroluminescence device)array plate 1 as a source of light which is directed onto the fingerprint of a finger, a prism 2, an image-forming lens system 3 for forming an image of a fingerprint on the inclined surface of the prism 2, an area charge coupled device (in short, an area CCD) 4 for converting the fingerprint image formed by the image-forming lens system 3 to electrical signals, and a circuit 5 for amplifying and analyzing the electrical signals from the area CCD 4.

When light is emitted from the LED array plate 1 onto the inclined surface of the prism 2 on which a finger makes contact, the above-mentioned fingerprint recognition device forms a fingerprint image on the inclined surface of the prism 2 by making the convex portions of the fingerprint of the finger bright since those portions contact the inclined surface of the prism 2 and making the concave portions of the fingerprint of the finger dark since the portions do not contact the inclined surface of the prism 2.

Such a fingerprint image is formed on the area CCD 4 by means of the image-forming lens system 3 and then is converted to electrical signals to be transferred to the circuit 5 in which the electrical signals are amplified and analyzed to recognize the fingerprint.

As indicated in FIG. 2, however, the above-mentioned conventional fingerprint recognition device forms a slanted fingerprint image 6 on the area CCD 4 since the fingerprint image is formed on the prism 2 in a 45°-slanted state with respect to the optical axis of the horizontally mounted image-forming lens system 3.

According to this, since the fingerprint image appears clearly around the optical axis but it becomes more defocused as one goes farther from the optical axis, the conventional fingerprint recognition device has problems in that image distortions and the like occur which make an accurate fingerprint recognition impossible.

And also, since the image-forming lens system 3 consists of a plurality of lenses in order to compensate for the above-mentioned problems to a certain extent, the conventional fingerprint recognition device has other problems in that as the volume of the optical system becomes larger, the manufacturing cost increases, and the like.

SUMMARY OF THE INVENTION

It is an object of the present invention to provide a fingerprint recognition device to solve the above-mentioned problems.

The fingerprint recognition device according to the present invention for achieving such an object has a configuration having a laser for emitting light, a collimator for making the light travel in parallel, and a tetragonal prism on which a fingerprint image is formed, are arranged along a first optical axis, and also a hologram for shifting the virtual position of said fingerprint image, an image-forming lens for forming a real fingerprint image, and an area CCD for converting the real fingerprint image into electrical signals are arranged along a second optical axis. The area CCD is connected to a circuit which amplifies and analyzes the electrical signals.

In the fingerprint recognition device according to the present invention, a real image of a fingerprint is transformed into a virtual image on the optical axis of the image-forming lens by means of the hologram. The virtual image is formed on the area CCD by means of the image-forming lens to generate electrical signals according to the fingerprint image. The electrical signals are then transferred to the circuit section which amplifies and analyzes the signals, and then the fingerprint is recognized.

Since a fingerprint image is recognized after the fingerprint image is shifted onto an optical axis of the image-forming lens by using the hologram, the above-mentioned fingerprint recognition device according to the present invention can enhance the reliability of a product by completely eliminating image distortion phenomena and recognition error factors and performing an accurate recognition.

DETAILED DESCRIPTION OF THE INVENTION

The present invention as described above will be described in detail below along with preferred embodiments with reference to FIGS. 3 and 4.

Figure 1:
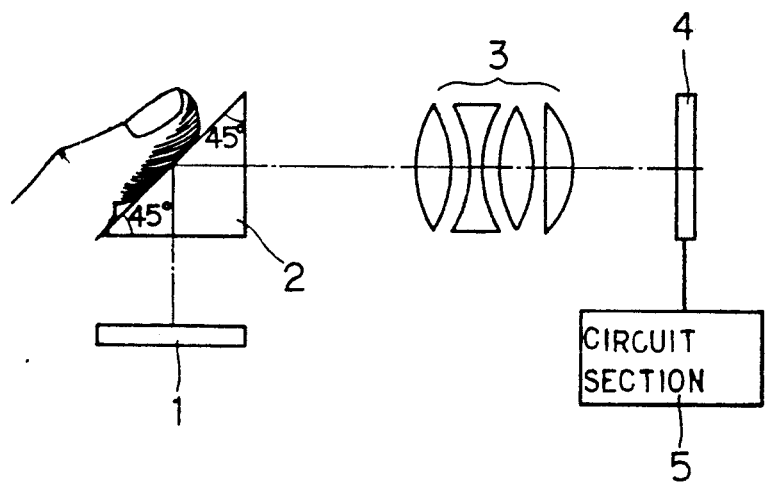
FIG. 1 shows a configurational view for an optical system of the conventional fingerprint recognition device.
Figure 2:
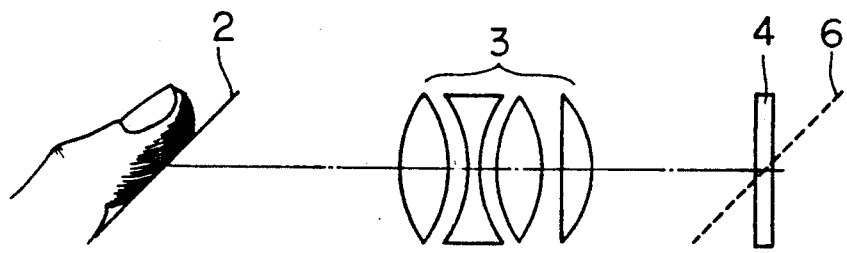
FIG. 2 shows a schematic operational view for operations of the conventional fingerprint recognition device.
Figure 3:
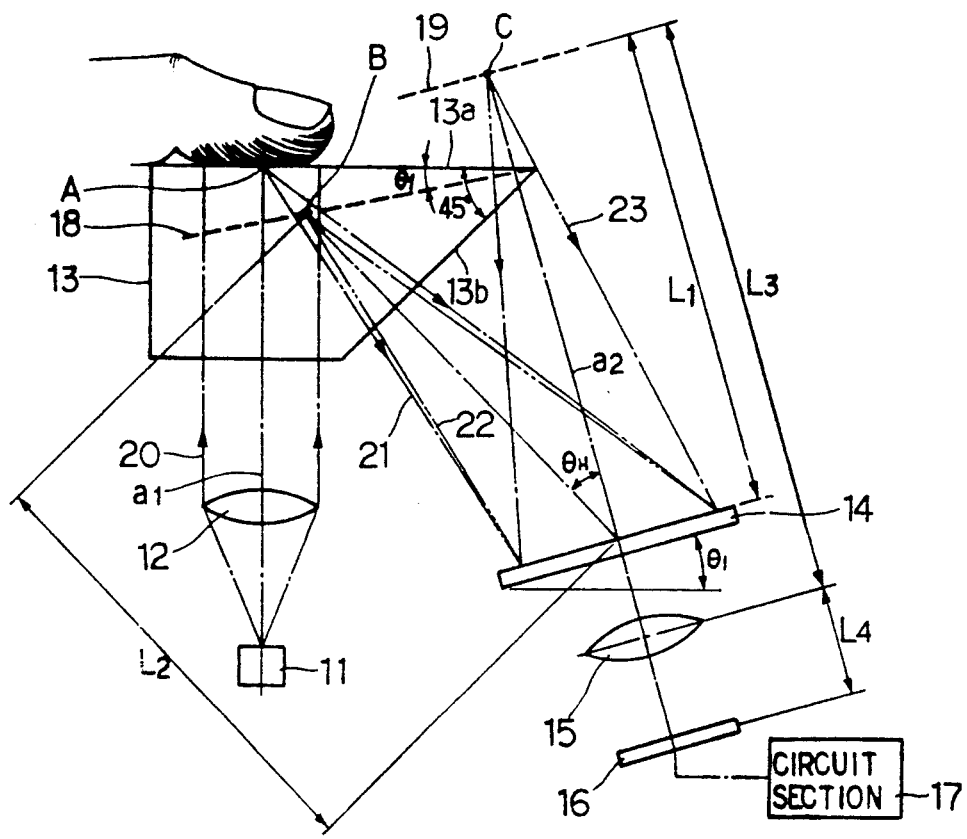
FIG. 3 shows a configurational view for an optical system of the fingerprint recognition device according to the present invention.

FIG. 3 shows a configurational view for the fingerprint recognition device according to the present invention.

As shown in FIG. 3, the present invention has a configuration that includes a laser 11 for generating a laser beam, a collimator 12 for making the laser beam from the laser 11 travel in parallel, and a tetragonal prism 13 for forming a fingerprint image are arranged along a first optical axis $a_1$. A hologram 14 is disposed in the reflected beam from the fingerprint to shift the position of the fingerprint image formed by the tetragonal prism 13 onto a second optical axis $a_2$. An image-forming lens 15 for forming a fingerprint image, and an area CCD 16 disposed at that fingerprint image for converting the fingerprint image formed by the image-forming lens 15 to electrical signals are also arranged along the second optical axis $a_2$. The area CCD 16 is connected to a circuit section 17 which amplifies and analyzes the electrical signals transferred therefrom. The diffused laser beam passes through the first image formation plane 18 along a third optical axis 22, which optical axis intercepts the second surface 13a of the prism 13 at point A, is orthogonal to the third prism surface 13b and intercepts hologram 14 at is surface at the point where the second optical axis 22 intercepts that surface.

A contact surface 13a of the tetragonal prism 13, on which a finger contacts is perpendicular to the first optical axis a, and an inclined surface 13b of the tetragonal prism 13 is arranged toward said hologram 14, wherein the inside angle between the contact surface 13a and the inclined surface 13b is 45°.

The laser beam incident on the tetragonal prism 13 from the collimator 12 allows a fingerprint image to be formed on the first image formation plane 18 forming a predetermined angle $\theta_1$ with respect to the contact surface 13a.

Figure 4:
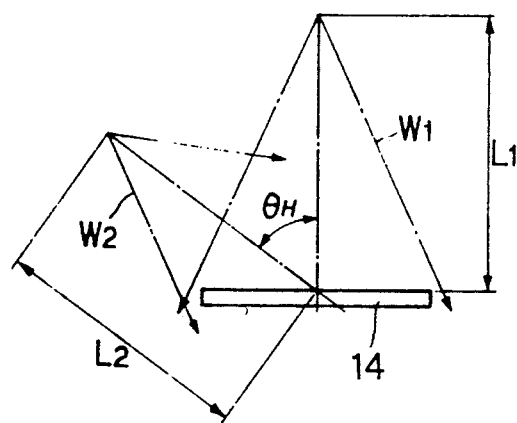
FIG. 4 shows an operational view of a hologram applied to the present invention.

As shown in FIG. 4, said hologram 14 is generated by interfering spherical waves $W_1$ and $W_2$ which are incident in a predetermined angle $\theta_H$ therebetween on the holographic plate, wherein said spherical wave $W_1$ is generated at a distance $L_1$ and said spherical wave $W_2$ is generated at a distance $L_2$ from the holographic plate 14.

Said $\theta_H$ has to satisfy an equation below:

$$\theta_H = 45° - \theta_1$$

Said $W_1$ is an object wave and said $W_2$ is a reference wave.

Said hologram 14 is arranged to be inclined in an angle of $\theta_1$ with respect to the horizontal plane making it parallel to, the first image formation plane 18 of the tetragonal prism 13. The hologram 14 is positioned of a distance $L_2$ from the first image formation plane 18 and a fingerprint image is formed by the laser beam incident on the hologram 14 from the tetragonal prism 13 on the second image formation plane 19 at a distance $L_1$ from said hologram 14.

Said image-forming lens 15 is arranged at a distance $L_3$ from said second image formation plane 19 and said area CCD 16 is arranged at a distance $L_4$ from the image-forming lens 15. With such an arrangement, a fingerprint image is formed on the area CCD 16 which is magnified $L_4/L_3$ times.

The optical axes of said hologram 14 and image-forming lens 15 are focused at the central point C of said second image formation plane 19. In the FIG. 3, reference numeral 20 denotes a laser beam made parallel by the collimator 12, the reference numeral 21 a laser beam diffused due to a fingerprint of a finger, the reference numeral 22 denotes a diffused laser beam which the position of the diffused laser beam 21 has moved due to the different degrees of brightness caused by the fingerprint on the tetragonal prism 13, and the reference numeral 23 denotes a virtual diffused laser beam to which the diffused laser beam 22 has been shifted by the hologram 14.

The operation and effect of the fingerprint recognition device according to the present invention having such a configuration will be described as follows.

As shown in FIG. 3, the laser beam from the laser 11 travels in parallel with the optical axis $a_1$ by the collimator 12 and reaches the portion of a finger contacted on the tetragonal prism 13.

The laser beam reaching the finger portion contacted on the prism 13 is diffused according to the convex-concave nature of the fingerprint of the finger portion and is reflected by or penetrates through the finger-noncontacted portions of the prism 13.

At this time, the laser beam, diffused according to the convex-concave portions of the fingerprint, forms a fingerprint image at the first image plane 18. In more detail, a fingerprint image is substantially formed due to the optical path length differences caused by the tetragonal prism 13 on the image formation plane 18 forming an angle of $\theta_1$ with respect to the finger-contacted surface 13a of the prism 13.

That is, the laser beam which is diffused at the point A of the tetragonal prism 13 substantially becomes the laser beam which is diffused at the point B of the first image formation plane 18.

The fingerprint image formed as described above travels on the hologram 14 and is shifted to the second image formation plane 19 by the hologram 14, so that the virtual fingerprint image is put on the optical axis $a_2$ of the image-forming lens 15.

According to this, the aberration caused by an object deviated from an optical axis are completely removed.

As mentioned above, the fingerprint image shifted onto the second optical axis $a_2$ is formed on the area CCD 16 by means of the image-forming lens 15.

At this time, the fingerprint image is formed on the area CCD 16 and is magnified by the factor $L_4/L_3$.

Hereinafter, the fingerprint image formed on the area CCD 16 is converted into electrical signals by the area CCD 16, as is performed in the conventional fingerprint recognition device. Then the electrical signals are amplified and analyzed by the circuit section 17 to recognize the fingerprint.

That is, the fingerprint recognition device according to the present invention is characterized in that image distortions are completely corrected by shifting a real image of a fingerprint image formed on the tetragonal prism 13 to the optical axis $a_2$ of the image-forming lens 15 by means of the hologram 14 in order to form a virtual image and forming the virtual image on the area CCD 16 by means of the image-forming lens 15.

As described above in detail, the fingerprint recognition device according to the present invention has the effect that a fingerprint image formed on the prism is more accurately recognized by using the hologram.

What is claimed is:

1. A fingerprint recognition device which is capable of improved recognition through the generation of an accurate distortion-free image of a fingerprint, the fingerprint recognition device comprising:
    a laser for emitting a laser beam along a first optical axis,
    a collimator disposed or the first optical axis for collecting the laser beam and directing the laser beam along and parallel with the first optical axis,
    a tetragonal prism having first and second parallel surfaces thereon and a third surface which is inclined to the first and second surfaces, the second prism surface being adapted to receive a finger thereon whose fingerprint it is desired to be recognized,
    the laser beam which is directed along the first optical axis being incident on and perpendicular to the first prism surface so that the collimated laser beam passes through the first prism surface to the second prism surface where it is diffused by the fingerprint thereon so as to form an image of the fingerprint within the tetragonal prism at a first image plane, which image plane is inclined to the second prism surface,
    the diffused laser beam being deflected by the second prism surface so to pass through the first image plane and orthogonally through the third prism surface along a third optical axis, a hologram disposed along the third optical axis so as to intercept the diffused laser beam from the first image plane, the hologram being disposed parallel to the first image plane and producing a distortion-free virtual image of the fingerprint at a second image formation plane, a central point of the virtual image and the intersection of the third optical axis with the hologram define a second optical axis, an image-forming lens aligned on the second optical axis for viewing the virtual image of the fingerprint through the hologram and for forming a real distortion-free image of the fingerprint, an area CCD disposed along and perpendicular to the second optical axis at the plane of the real distortion-free image formed by the image-forming lens to convert that fingerprint image into electrical signals, and a circuit connected to the area CCD for amplifying and analyzing these electrical signals, whereby improved fingerprint identification is accomplished because the area CCD is presented with a distortion-free image produced by the hologram.

2. A fingerprint recognition device as claimed in claim 1, wherein said hologram is generated by an object wave and a reference wave both incident on the hologram at an angle $\theta_H$ which is the same as an angle formed between the third optical axis and the second optical axis on the holographic plate, said object wave and reference wave being generated at distances L1 and L2 from said holographic plate, respectively.

3. A fingerprint recognition device as claimed in claim 2, wherein the inside angle between the second contact surface to which a finger contacts and the third inclined surface faced toward said hologram in said tetragonal prism is 45°, said object plane is formed to be inclined in a predetermined angle $\theta_1$ ($\theta_1 < 45°$) with respect to said second contact surface, which angle depends on the refractive index of material of said tetragonal prism, and said hologram is inclined in clockwise direction at an angle of $\theta_H$ with respect to said third optical axis at distance L2, and said virtual image is located at distance L1 above said hologram.

4. A fingerprint recognition device as claimed in claim 3, wherein said image-forming lens is located at distance L3 (L3>L1) from said virtual image position along said second optical axis, and said area CCD is located at distance L4 from said image-forming lens along said second optical axis in order to form a fingerprint image which is L4/L3 times as large as said virtual image on said area CCD.

5. A fingerprint recognition device as claimed in one of claims 3 and 4, wherein said angle $\theta_H$ is set to satisfy the equation $\theta_H = 45° - \theta_1$.

* * * * *